US012208220B2

(12) United States Patent
Komp et al.

(10) Patent No.: US 12,208,220 B2
(45) Date of Patent: *Jan. 28, 2025

(54) ACTIVE DISTAL TIP DRIVE

(71) Applicant: Covidien LP, Mansfield, MA (US)

(72) Inventors: John W. Komp, Dillon, CO (US); Scott E. M. Frushour, Boulder, CO (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/206,913

(22) Filed: Jun. 7, 2023

(65) Prior Publication Data
US 2023/0310805 A1 Oct. 5, 2023

Related U.S. Application Data

(63) Continuation of application No. 17/307,790, filed on May 4, 2021, now Pat. No. 11,701,492.

(Continued)

(51) Int. Cl.
*A61B 5/00* (2006.01)
*A61B 6/12* (2006.01)
(Continued)

(52) U.S. Cl.
CPC ........... *A61M 25/0105* (2013.01); *A61B 6/12* (2013.01); *A61B 8/0841* (2013.01); *A61B 34/20* (2016.02);
(Continued)

(58) Field of Classification Search
CPC .... A61M 25/0105; A61B 34/20; A61B 34/25; A61B 2034/2048; A61B 2034/2065; A61B 2017/00699; A61B 2017/00703
See application file for complete search history.

(56) References Cited

U.S. PATENT DOCUMENTS

| 4,202,352 A | 5/1980 | Osborn |
| 5,358,496 A | 10/1994 | Ortiz et al. |
| (Continued) | | |

FOREIGN PATENT DOCUMENTS

| BR | 0013237 A | 7/2003 |
| BR | 0116004 A | 6/2004 |
| (Continued) | | |

OTHER PUBLICATIONS

Communication pursuant to Article 94(3) EPC issued in European Patent No. 21177547.3 dated Jun. 9, 2023.

(Continued)

*Primary Examiner* — Joel F Brutus
(74) *Attorney, Agent, or Firm* — Weber Rosselli & Cannon LLP

(57) ABSTRACT

A method and system of correcting alignment of catheter relative to a target including receiving signals from an inertial measurement unit located at a distal end of a catheter, determining movement of the distal end of the catheter caused by physiological forces, receiving images depicting the distal end of the catheter and the target, identifying the distal end of the catheter and the target in the images, determining an orientation of the distal end of the catheter relative to the target and articulating the distal tip of the catheter in response to the detected movement to achieve and maintain an orientation towards the target such that a tool extended from an opening at the distal end of the catheter would intersect the target.

20 Claims, 7 Drawing Sheets

Related U.S. Application Data

(60) Provisional application No. 63/034,501, filed on Jun. 4, 2020.

(51) Int. Cl.
*A61B 8/08* (2006.01)
*A61B 34/00* (2016.01)
*A61B 34/20* (2016.01)
*A61M 25/01* (2006.01)
*A61B 17/00* (2006.01)

(52) U.S. Cl.
CPC .... *A61B 34/25* (2016.02); *A61B 2017/00699* (2013.01); *A61B 2017/00703* (2013.01); *A61B 2034/2048* (2016.02); *A61B 2034/2065* (2016.02); *A61M 2025/0166* (2013.01)

(56) References Cited

U.S. PATENT DOCUMENTS

| | | | |
|---|---|---|---|
| 6,086,586 A | 7/2000 | Hooven | |
| 6,493,575 B1 | 12/2002 | Kesten et al. | |
| 6,533,784 B2 | 3/2003 | Truckai et al. | |
| 6,656,177 B2 | 12/2003 | Truckai et al. | |
| 6,802,843 B2 | 10/2004 | Truckai et al. | |
| 6,835,336 B2 | 12/2004 | Watt | |
| 6,913,579 B2 | 7/2005 | Truckai et al. | |
| 7,806,891 B2 | 10/2010 | Nowlin et al. | |
| 7,947,000 B2 | 5/2011 | Vargas et al. | |
| 8,052,636 B2 | 11/2011 | Moll et al. | |
| 8,190,238 B2 | 5/2012 | Moll et al. | |
| 8,600,551 B2 | 12/2013 | Itkowitz et al. | |
| 8,668,638 B2 | 3/2014 | Donhowe et al. | |
| 8,900,131 B2 | 12/2014 | Chopra et al. | |
| 8,914,150 B2 | 12/2014 | Moll et al. | |
| 9,119,654 B2 | 9/2015 | Ramans et al. | |
| 9,283,049 B2 | 3/2016 | Diolaiti et al. | |
| 9,393,000 B2 | 7/2016 | Donhowe | |
| 9,500,473 B2 | 11/2016 | Ramamurthy et al. | |
| 9,801,630 B2 | 10/2017 | Harris et al. | |
| 9,839,481 B2 | 12/2017 | Blumenkranz et al. | |
| 9,993,313 B2 | 6/2018 | Schuh et al. | |
| 10,022,192 B1 | 7/2018 | Ummalaneni | |
| 10,130,345 B2 | 11/2018 | Wong et al. | |
| 10,143,526 B2 | 12/2018 | Walker et al. | |
| 10,172,973 B2 | 1/2019 | Vendely et al. | |
| 10,206,686 B2 | 2/2019 | Swayze et al. | |
| 10,231,788 B2 | 3/2019 | Olson et al. | |
| 10,299,870 B2 | 5/2019 | Connolly et al. | |
| 10,314,463 B2 | 6/2019 | Agrawal et al. | |
| 10,349,938 B2 | 7/2019 | Widenhouse et al. | |
| 10,368,951 B2 | 8/2019 | Moll et al. | |
| 10,482,599 B2 | 11/2019 | Mintz et al. | |
| 10,539,478 B2 | 1/2020 | Lin et al. | |
| 10,543,048 B2 | 1/2020 | Noonan | |
| 10,631,949 B2 | 4/2020 | Schuh et al. | |
| 10,638,953 B2 | 5/2020 | Duindam et al. | |
| 10,639,108 B2 | 5/2020 | Romo et al. | |
| 10,653,866 B2 | 5/2020 | Duindam et al. | |
| 10,667,871 B2 | 6/2020 | Romo et al. | |
| 10,667,875 B2 | 6/2020 | DeFonzo et al. | |
| 10,682,192 B2 | 6/2020 | Fenech | |
| 10,716,637 B2 | 7/2020 | Kowshik et al. | |
| 10,729,886 B2 | 8/2020 | Fenech et al. | |
| 10,743,751 B2 | 8/2020 | Landey et al. | |
| 10,744,303 B2 | 8/2020 | Duindam et al. | |
| 10,751,140 B2 | 8/2020 | Wallace et al. | |
| 10,765,303 B2 | 9/2020 | Graetzel et al. | |
| 10,765,487 B2 | 9/2020 | Ho et al. | |
| 10,779,803 B2 | 9/2020 | Prisco et al. | |
| 10,779,898 B2 | 9/2020 | Hill et al. | |
| 10,786,329 B2 | 9/2020 | Schuh et al. | |
| 10,792,022 B2 | 10/2020 | Keast et al. | |
| 10,792,464 B2 | 10/2020 | Romo et al. | |
| 10,813,539 B2 | 10/2020 | Graetzel et al. | |
| 10,820,947 B2 | 11/2020 | Julian | |
| 10,820,954 B2 | 11/2020 | Marsot et al. | |
| 10,842,575 B2 | 11/2020 | Panescu et al. | |
| 10,842,581 B2 | 11/2020 | Bailey | |
| 10,849,591 B2 | 12/2020 | Azizian et al. | |
| 10,850,013 B2 | 12/2020 | Hsu et al. | |
| 10,856,855 B2 | 12/2020 | Gordon | |
| 10,881,280 B2 | 1/2021 | Baez, Jr. | |
| 10,881,385 B2 | 1/2021 | Fenech | |
| 2005/0107808 A1 | 5/2005 | Evans et al. | |
| 2005/0165276 A1 | 7/2005 | Belson et al. | |
| 2006/0235457 A1 | 10/2006 | Belson | |
| 2007/0135803 A1 | 6/2007 | Belson | |
| 2013/0096385 A1 | 4/2013 | Fenech et al. | |
| 2013/0096572 A1 | 4/2013 | Donhowe et al. | |
| 2014/0052018 A1 | 2/2014 | Hawkins | |
| 2014/0235943 A1 | 8/2014 | Paris et al. | |
| 2016/0001038 A1 | 1/2016 | Romo et al. | |
| 2016/0067450 A1 | 3/2016 | Kowshik | |
| 2016/0128669 A1 | 5/2016 | Hill et al. | |
| 2016/0256230 A1 | 9/2016 | Kowshik et al. | |
| 2016/0270865 A1 | 9/2016 | Landey et al. | |
| 2016/0270870 A1 | 9/2016 | Kowshik | |
| 2016/0331358 A1 | 11/2016 | Gordon | |
| 2016/0338783 A1 | 11/2016 | Romo et al. | |
| 2016/0374676 A1 | 12/2016 | Flanagan et al. | |
| 2017/0020628 A1 | 1/2017 | Averbuch | |
| 2017/0112366 A1 | 4/2017 | Duindam et al. | |
| 2017/0112588 A1 | 4/2017 | Bissing et al. | |
| 2017/0151026 A1 | 6/2017 | Panescu et al. | |
| 2017/0156685 A1 | 6/2017 | Dickhans et al. | |
| 2017/0224338 A1 | 8/2017 | Sung | |
| 2017/0238795 A1 | 8/2017 | Blumenkranz et al. | |
| 2017/0258309 A1 | 9/2017 | Deyanov | |
| 2017/0273542 A1 | 9/2017 | Au | |
| 2017/0273712 A1 | 9/2017 | Carlson et al. | |
| 2017/0274189 A1 | 9/2017 | Smith et al. | |
| 2017/0281287 A1 | 10/2017 | Au | |
| 2017/0281288 A1 | 10/2017 | Au | |
| 2017/0325896 A1 | 11/2017 | Donhowe et al. | |
| 2018/0001058 A1 | 1/2018 | Schlesinger | |
| 2018/0027985 A1 | 2/2018 | Gallaga et al. | |
| 2018/0056040 A1 | 3/2018 | Fenech et al. | |
| 2018/0064904 A1 | 3/2018 | Vargas et al. | |
| 2018/0070935 A1 | 3/2018 | Fenech | |
| 2018/0214011 A1 | 8/2018 | Graetzel et al. | |
| 2018/0214138 A9 | 8/2018 | Prisco et al. | |
| 2018/0221038 A1 | 8/2018 | Noonan et al. | |
| 2018/0221039 A1 | 8/2018 | Shah | |
| 2018/0235565 A1 | 8/2018 | Azizian et al. | |
| 2018/0280660 A1 | 10/2018 | Landey et al. | |
| 2018/0325499 A1 | 11/2018 | Andey et al. | |
| 2019/0000568 A1 | 1/2019 | Connolly et al. | |
| 2019/0000576 A1 | 1/2019 | Mintz et al. | |
| 2019/0076143 A1 | 3/2019 | Smith | |
| 2019/0133702 A1 | 5/2019 | Fenech et al. | |
| 2019/0167366 A1 | 6/2019 | Ummalaneni et al. | |
| 2019/0167367 A1 | 6/2019 | Walker et al. | |
| 2019/0192143 A1 | 6/2019 | Shelton, IV et al. | |
| 2019/0192819 A1 | 6/2019 | Duindam et al. | |
| 2019/0200984 A1 | 7/2019 | Shelton, IV et al. | |
| 2019/0216447 A1 | 7/2019 | Bailey et al. | |
| 2019/0223693 A1 | 7/2019 | Vargas | |
| 2019/0223759 A1 | 7/2019 | Page et al. | |
| 2019/0231449 A1 | 8/2019 | Diolaiti et al. | |
| 2019/0239724 A1 | 8/2019 | Averbuch et al. | |
| 2019/0246876 A1 | 8/2019 | Schaning | |
| 2019/0246882 A1 | 8/2019 | Graetzel et al. | |
| 2019/0247128 A1 | 8/2019 | Inouye et al. | |
| 2019/0262086 A1 | 8/2019 | Connolly et al. | |
| 2019/0269468 A1 | 9/2019 | Hsu et al. | |
| 2019/0269885 A1 | 9/2019 | Bailey et al. | |
| 2019/0290109 A1 | 9/2019 | Agrawal et al. | |
| 2019/0290375 A1 | 9/2019 | Dearden et al. | |
| 2019/0298460 A1 | 10/2019 | Al-Jadda et al. | |
| 2019/0298465 A1 | 10/2019 | Chin et al. | |
| 2019/0328213 A1 | 10/2019 | Landey et al. | |
| 2019/0350660 A1 | 11/2019 | Moll et al. | |
| 2019/0350662 A1 | 11/2019 | Huang et al. | |

(56) References Cited

U.S. PATENT DOCUMENTS

| | | |
|---|---|---|
| 2019/0365201 A1 | 12/2019 | Noonan et al. |
| 2019/0374297 A1 | 12/2019 | Wallace et al. |
| 2020/0000533 A1 | 1/2020 | Schuh et al. |
| 2020/0000537 A1 | 1/2020 | Marsot et al. |
| 2020/0008678 A1 | 1/2020 | Barbagli et al. |
| 2020/0008827 A1 | 1/2020 | Dearden et al. |
| 2020/0008874 A1 | 1/2020 | Barbagli et al. |
| 2020/0022762 A1 | 1/2020 | Cassell et al. |
| 2020/0022767 A1 | 1/2020 | Hill et al. |
| 2020/0029948 A1 | 1/2020 | Wong et al. |
| 2020/0030575 A1 | 1/2020 | Bogusky et al. |
| 2020/0038123 A1 | 2/2020 | Graetzel et al. |
| 2020/0039086 A1 | 2/2020 | Meyer et al. |
| 2020/0046434 A1 | 2/2020 | Graetzel et al. |
| 2020/0060512 A1 | 2/2020 | Holsing et al. |
| 2020/0060516 A1 | 2/2020 | Baez, Jr. |
| 2020/0069384 A1 | 3/2020 | Fenech et al. |
| 2020/0077991 A1 | 3/2020 | Gordon et al. |
| 2020/0078096 A1 | 3/2020 | Barbagli et al. |
| 2020/0078103 A1* | 3/2020 | Duindam ............... A61B 90/37 |
| 2020/0078104 A1 | 3/2020 | Bailey et al. |
| 2020/0085516 A1 | 3/2020 | DeFonzo et al. |
| 2020/0093549 A1 | 3/2020 | Chin et al. |
| 2020/0093554 A1 | 3/2020 | Schuh et al. |
| 2020/0100776 A1 | 4/2020 | Blumenkranz et al. |
| 2020/0100845 A1 | 4/2020 | Julian |
| 2020/0100853 A1 | 4/2020 | Ho et al. |
| 2020/0100855 A1 | 4/2020 | Leparmentier et al. |
| 2020/0107894 A1 | 4/2020 | Wallace et al. |
| 2020/0107899 A1 | 4/2020 | Carlson et al. |
| 2020/0121170 A1 | 4/2020 | Gordon et al. |
| 2020/0146757 A1 | 5/2020 | Fenech et al. |
| 2020/0163581 A1 | 5/2020 | Kowshik et al. |
| 2020/0163726 A1 | 5/2020 | Tanner et al. |
| 2020/0171660 A1 | 6/2020 | Ho et al. |
| 2020/0197112 A1 | 6/2020 | Chin et al. |
| 2020/0198147 A1 | 6/2020 | Fredrickson et al. |
| 2020/0205908 A1 | 7/2020 | Julian et al. |
| 2020/0206472 A1 | 7/2020 | Ma et al. |
| 2020/0217733 A1 | 7/2020 | Lin et al. |
| 2020/0222134 A1 | 7/2020 | Schuh et al. |
| 2020/0222666 A1 | 7/2020 | Chan et al. |
| 2020/0237458 A1 | 7/2020 | DeFonzo et al. |
| 2020/0253670 A1 | 8/2020 | Doisneau et al. |
| 2020/0254223 A1 | 8/2020 | Duindam et al. |
| 2020/0261172 A1 | 8/2020 | Romo et al. |
| 2020/0261175 A1 | 8/2020 | Fenech |
| 2020/0268240 A1 | 8/2020 | Blumenkranz et al. |
| 2020/0268459 A1 | 8/2020 | Noonan |
| 2020/0268463 A1 | 8/2020 | Au |
| 2020/0275984 A1 | 9/2020 | Brisson et al. |
| 2020/0281787 A1 | 9/2020 | Ruiz |
| 2020/0289023 A1 | 9/2020 | Duindam et al. |
| 2020/0297437 A1 | 9/2020 | Schuh et al. |
| 2020/0305983 A1 | 10/2020 | Yampolsky et al. |
| 2020/0305989 A1 | 10/2020 | Schuh et al. |
| 2020/0323593 A1 | 10/2020 | Coste-Maniere et al. |
| 2020/0330167 A1 | 10/2020 | Romo et al. |
| 2020/0345436 A1 | 11/2020 | Kowshik et al. |
| 2020/0352420 A1 | 11/2020 | Graetzel et al. |
| 2020/0352427 A1 | 11/2020 | Deyanov |
| 2020/0352675 A1 | 11/2020 | Averbuch |
| 2020/0367719 A1 | 11/2020 | Au |
| 2020/0367726 A1 | 11/2020 | Landey et al. |
| 2020/0367981 A1 | 11/2020 | Ho et al. |
| 2020/0375678 A1 | 12/2020 | Wallace et al. |
| 2020/0383750 A1 | 12/2020 | Kemp et al. |
| 2020/0391010 A1 | 12/2020 | Fenech et al. |
| 2020/0405317 A1 | 12/2020 | Wallace |
| 2020/0405411 A1 | 12/2020 | Draper et al. |
| 2020/0405419 A1 | 12/2020 | Mao et al. |
| 2020/0405420 A1 | 12/2020 | Purohit et al. |
| 2020/0405423 A1 | 12/2020 | Schuh |
| 2020/0405424 A1 | 12/2020 | Schuh |
| 2020/0405434 A1 | 12/2020 | Schuh et al. |
| 2020/0406002 A1 | 12/2020 | Romo et al. |
| 2022/0160335 A1 | 5/2022 | Matsumoto |

FOREIGN PATENT DOCUMENTS

| | | |
|---|---|---|
| CZ | 2486540 B6 | 9/2016 |
| CZ | 3060157 A | 12/2019 |
| EP | 3326551 A1 | 5/2018 |
| EP | 3367915 A4 | 7/2019 |
| EP | 3562423 A1 | 11/2019 |
| EP | 3552653 A3 | 12/2019 |
| EP | 3576598 A1 | 12/2019 |
| EP | 3576599 A1 | 12/2019 |
| EP | 3644820 A1 | 5/2020 |
| EP | 3645100 A1 | 5/2020 |
| EP | 3654870 A2 | 5/2020 |
| EP | 3668582 A2 | 6/2020 |
| EP | 3576599 A4 | 11/2020 |
| MX | PA03005028 A | 1/2004 |
| MX | 225663 B | 1/2005 |
| MX | 226292 B | 2/2005 |
| MX | 246862 B | 6/2007 |
| MX | 265247 B | 3/2009 |
| MX | 284569 B | 3/2011 |

OTHER PUBLICATIONS

The Extended European Search Report issued in European Patent Application No. 21177547.3 dated Oct. 29, 2021.

* cited by examiner

ACTIVE DISTAL TIP DRIVE

CROSS-REFERENCE TO RELATED APPLICATION

This application is a continuation of U.S. patent application Ser. No. 17/307,790, filed on May 4, 2021, which claims the benefit of and priority to U.S. Provisional Patent Application No. 63/034,501, filed on Jun. 4, 2020, the entire disclosure of each of which is incorporated by reference herein.

BACKGROUND

Technical Field

This disclosure relates to the field of navigation of and maintaining position of medical devices, such as biopsy or ablation tools, relative to targets.

Description of Related Art

There are several commonly applied medical methods, such as endoscopic procedures or minimally invasive procedures, for treating various maladies affecting organs including the liver, brain, heart, lungs, gall bladder, kidneys, and bones. Often, one or more imaging modalities, such as magnetic resonance imaging (MRI), ultrasound imaging, computed tomography (CT), or fluoroscopy are employed by clinicians to identify and navigate to areas of interest within a patient and ultimately a target for biopsy or treatment. In some procedures, pre-operative scans may be utilized for target identification and intraoperative guidance. However, real-time imaging may be required to obtain a more accurate and current image of the target area. Furthermore, real-time image data displaying the current location of a medical device with respect to the target and its surroundings may be needed to navigate the medical device to the target in a safe and accurate manner (e.g., without causing damage to other organs or tissue).

For example, an endoscopic approach has proven useful in navigating to areas of interest within a patient, and particularly so for areas within luminal networks of the body such as the lungs, blood vessels, colorectal cavities, and the renal ducts. To enable the endoscopic approach, navigation systems have been developed that use previously acquired MM data or CT image data to generate a three-dimensional (3D) rendering, model, or volume of the particular body part.

The resulting volume generated from the MRI scan or CT scan may be utilized to create a navigation plan to facilitate the advancement of a navigation catheter (or other suitable medical device) through the luminal network to an area of interest. A locating or tracking system, such as an electromagnetic (EM) tracking system or shape sensing tracking system, may be utilized in conjunction with, for example, CT data, to facilitate guidance of the navigation catheter to the area of interest.

However, once a catheter is navigated to a desired location the position of the catheter within the patient is constantly in flux. Change in position of the catheter may be caused by the movement of tools through the catheter, movement of the lungs themselves during respiration, and movement caused by the proximity of the lungs to the heart which is in constant motion as part of the cardiac process. Accordingly, improvements to current systems are desired.

SUMMARY

One aspect of the disclosure is directed to a method of maintaining orientation of a catheter relative to a target including: navigating a catheter in a luminal network, collecting data relating to movement of a distal tip of the catheter caused by physiological forces. The method of maintaining orientation also includes receiving images depicting the distal tip of the catheter and the target. The method of maintaining orientation also includes identifying the distal tip of the catheter and the target in the images. The method of maintaining orientation also includes determining an orientation of the distal tip of the catheter relative to the target. The method of maintaining orientation also includes confirming that the distal tip is oriented at the target. The method of maintaining orientation also includes articulating the distal tip of the catheter to maintain the orientation at the target based on the collected data. Other embodiments of this aspect include corresponding computer systems, apparatus, and computer programs recorded on one or more computer storage devices, each configured to perform the actions of the methods and systems described herein.

Implementations of this aspect of the disclosure may include one or more of the following features. The method where the collected data is received from an inertial measurement unit. The method further including determining a three-dimensional angle between a current orientation of the distal tip of the catheter and an orientation where a vector extending from the distal tip of the catheter intersect the target. The method further including articulating the distal tip of the catheter to achieve the orientation where the vector extending from the distal tip of the catheter intersect the target. The method where the images are fluoroscopic images. The method where the images are ultrasound images. The method where the physiological forces are caused by respiration and cardiac functions. The method where the data is collected during navigation of the catheter towards the target. The method further including presenting on a user interface a virtual catheter tip and a virtual target. The method further including presenting an indicator on the user interface when the physiological forces are in approximately the same phase of their cycle as when the distal tip was confirmed oriented at the target. Implementations of the described techniques may include hardware, a method or process, or computer software on a computer-accessible medium, including software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

Another aspect of the disclosure is directed to a method of correcting alignment of catheter relative to a target including: receiving signals from an inertial measurement unit located at a distal end of a catheter, determining movement of the distal end of the catheter caused by physiological forces. The method of correcting alignment of catheter also includes receiving images depicting the distal end of the catheter and the target. The method of correcting alignment of catheter also includes identifying the distal end of the catheter and the target in the images. The method of correcting alignment of catheter also includes determining an orientation of the distal end of the catheter relative to the target. The method of correcting alignment of catheter also includes articulating the distal tip of the catheter to achieve and maintain an orientation towards the target such that a tool extended from an opening at the distal end of the catheter would intersect the target. Other embodiments of this aspect include corresponding computer systems, apparatus, and computer programs recorded on one or more computer storage devices, each configured to perform the actions of the methods and systems described herein.

Implementations of this aspect of the disclosure may include one or more of the following features. The method further including determining a three-dimensional angle between a current orientation of the distal end of the catheter and an orientation where a vector extending from the distal end of the catheter intersect the target. The method where the images are fluoroscopic images. The method where the images are ultrasound images. The method where the physiological forces are caused by respiration and cardiac functions. The method where the data is collected during navigation of the catheter towards the target. Implementations of the described techniques may include hardware, a method or process, or computer software on a computer-accessible medium, including software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

A further aspect of the disclosure is directed to a system for maintaining orientation of a catheter towards a target including: a catheter including an inertial measurement unit (IMU), the IMU configured to generate signals relating to movement of the distal portion of the catheter, and a drive mechanism configured to articulate the distal portion of the catheter; and a computing device, the computing device including a processor and memory, the memory storing thereon instructions that when executed by the processor, receive signals from the IMU; determine motion of the IMU caused by physiological forces; receive images depicting the distal portion of the catheter and a target; determine the orientation of the distal portion of the catheter relative to the target based on the images; and send signals to the drive mechanism to articulating the distal portion of the catheter to achieve and maintain an orientation towards the target such that a tool extended from an opening at the distal portion of the catheter would intersect the target. Other embodiments of this aspect include corresponding computer systems, apparatus, and computer programs recorded on one or more computer storage devices, each configured to perform the actions of the methods and systems described herein.

Implementations of this aspect of the disclosure may include one or more of the following features. The system where the memory stores thereon instructions that when executed by the processor, determine a three-dimensional angle between a current orientation of the distal portion of the catheter and an orientation where a vector extending from the distal portion of the catheter intersect the target. The system where the movement of the distal portion of the catheter is a result of physiological forces including respiration and cardiac function. The system where the received images are fluoroscopic images. Implementations of the described techniques may include hardware, a method or process, or computer software on a computer-accessible medium, including software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

BRIEF DESCRIPTION OF THE DRAWINGS

Various aspects and embodiments of the disclosure are described hereinbelow with references to the drawings, wherein.

DETAILED DESCRIPTION

Catheters and catheter like devices, such as endoscopes, are used in a myriad of medical procedures. These flexible devices are typically used to navigate through luminal networks of the body including the vasculature, airways, and digestive systems. In accordance with the disclosure, to aide in navigating to a specific location, the distal tip of the catheter can be articulated, deflected, or rotated by a user through controls on the catheter proximal end outside the body. These manipulations allow the tip to point towards and enter branching structures. Upon arrival at the desired anatomic location a medical procedure may be performed such as lesion observation, heart valve replacement, stent or pacemaker deployment, radio frequency or microwave ablation, placement of chemotherapy drugs, and a variety of others.

In accordance with the disclosure, a 3D model of a patient's lungs or another suitable portion of the anatomy, may be generated from previously acquired scans, such as CT or MRI scans. The 3D model and related scan data are used to identify targets, e.g., potential lesions for biopsy or treatment, and to generate a pathway plan through the anatomy to reach the targets.

Once the pathway plan is generated and accepted by a clinician, that pathway plan may be utilized by a navigation system to drive a catheter or catheter like device along the pathway plan through the anatomy to reach the desired target. The driving of the catheter along the pathway plan may be manual or it may be robotic, or a combination of both. Manual systems include the ILLUMISITE navigation system sold by Medtronic PLC, robotic systems include the ION system sold by Intuitive Surgical Inc. and the MONARCH system sold by Auris Health, Inc. In a single procedure planning, registration of the pathway plan to the patient, and navigation are performed to enable a medical device, e.g., a catheter to be navigated along the planned path to reach a target, e.g., a lesion, so that a biopsy or treatment of the target can be completed.

Figure 1:
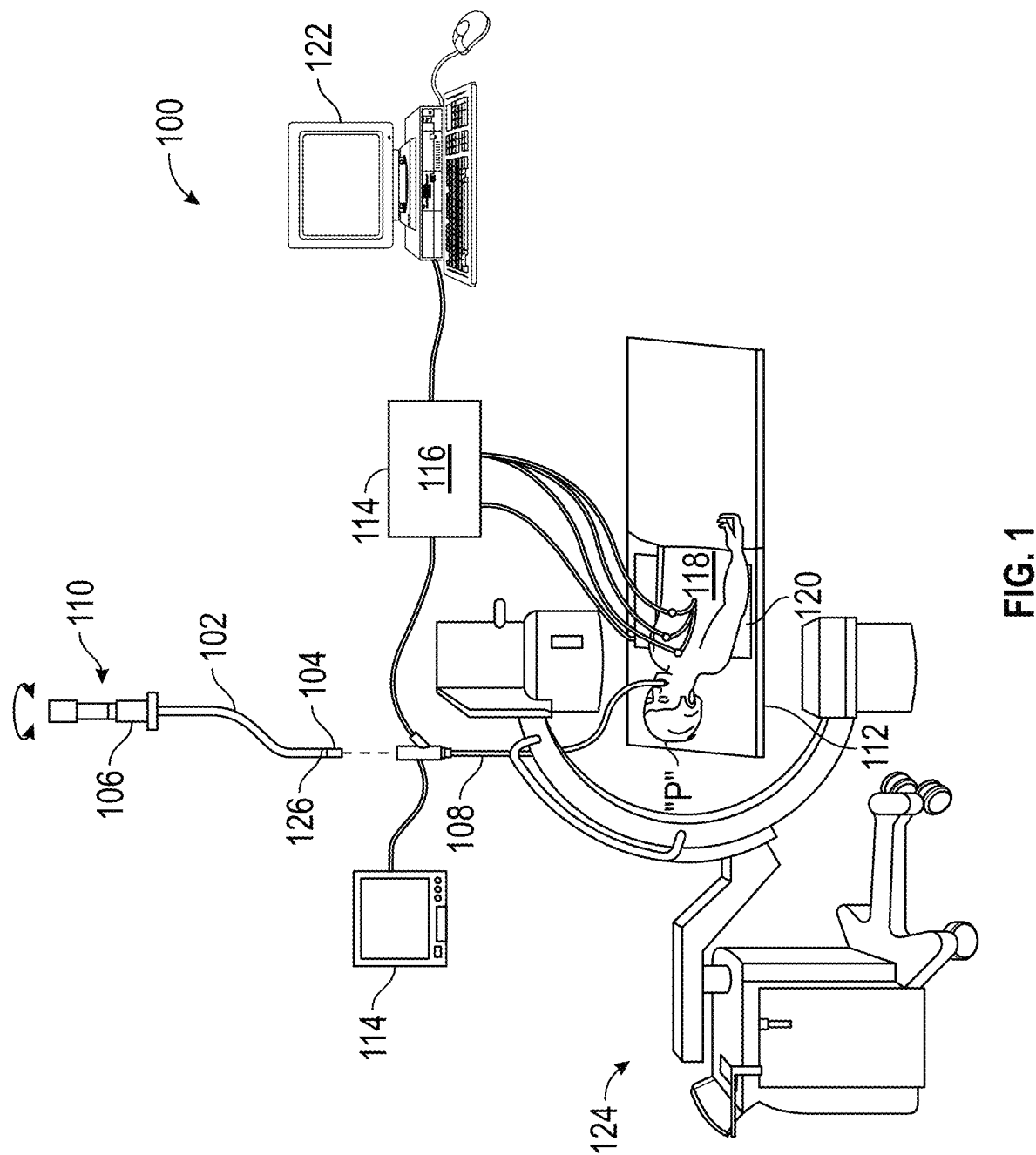
FIG. 1 is a schematic view of a luminal network navigation system in accordance with the disclosure.

FIG. 1 is a perspective view of an exemplary system for facilitating navigation of a medical device, e.g., a catheter to a soft-tissue target via airways of the lungs. System 100 may be further configured to construct fluoroscopic based three-dimensional volumetric data of the target area from 2D fluoroscopic images to confirm navigation to a desired location. System 100 may be further configured to facilitate approach of a medical device to the target area by using Electromagnetic Navigation (EMN) and for determining the location of a medical device with respect to the target. One such EMN system is the ILLUMISITE system currently sold by Medtronic PLC, though other systems for intraluminal navigation are considered within the scope of the disclosure including shape sensing technology which detect the shape of the distal portion of the catheter and match that shape to the shape of the luminal network in a 3D model.

One aspect of the system 100 is a software component for reviewing of computed tomography (CT) image scan data that has been acquired separately from system 100. The review of the CT image data allows a user to identify one or more targets, plan a pathway to an identified target (planning phase), navigate a catheter 102 to the target (navigation phase) using a user interface on computing device 122, and confirming placement of a sensor 104 relative to the target. The target may be tissue of interest identified by review of the CT image data during the planning phase. Following navigation, a medical device, such as a biopsy tool or other tool, may be inserted into catheter 102 to obtain a tissue sample from the tissue located at, or proximate to, the target.

As shown in FIG. 1, catheter 102 is part of a catheter guide assembly 106. In one embodiment, catheter 102 is inserted into a bronchoscope 108 for access to a luminal network of the patient P. Specifically, catheter 102 of catheter guide assembly 106 may be inserted into a working channel of bronchoscope 108 for navigation through a patient's luminal network. The he catheter 102 may itself include imaging capabilities and the bronchoscope 108 is not strictly required. A locatable guide (LG) 110 (a second catheter), including a sensor 104 may be inserted into catheter 102 and locked into position such that sensor 104 extends a desired distance beyond the distal tip of catheter 102. The position and orientation of sensor 104 relative to a reference coordinate system, and thus the distal portion of catheter 102, within an electromagnetic field can be derived. Catheter guide assemblies 106 are currently marketed and sold by Medtronic PLC under the brand names SUPERDIMENSION® Procedure Kits, or EDGE™ Procedure Kits, and are contemplated as useable with the disclosure.

System 100 generally includes an operating table 112 configured to support a patient P, a bronchoscope 108 configured for insertion through patient P's mouth into patient P's airways; monitoring equipment 114 coupled to bronchoscope 108 or catheter 102 (e.g., a video display, for displaying the video images received from the video imaging system of bronchoscope 108 or the catheter 102); a locating or tracking system 114 including a locating module 116, a plurality of reference sensors 18 and a transmitter mat 120 including a plurality of incorporated markers; and a computing device 122 including software and/or hardware used to facilitate identification of a target, pathway planning to the target, navigation of a medical device to the target, and/or confirmation and/or determination of placement of catheter 102, or a suitable device therethrough, relative to the target.

In accordance with aspects of the disclosure, the visualization of intra-body navigation of a medical device, e.g., a biopsy tool, towards a target, e.g., a lesion, may be a portion of a larger workflow of a navigation system. A fluoroscopic imaging device 124 capable of acquiring fluoroscopic or x-ray images or video of the patient P is also included in this particular aspect of system 100. The images, sequence of images, or video captured by fluoroscopic imaging device 124 may be stored within fluoroscopic imaging device 124 or transmitted to computing device 122 for storage, processing, and display. Additionally, fluoroscopic imaging device 124 may move relative to the patient P so that images may be acquired from different angles or perspectives relative to patient P to create a sequence of fluoroscopic images, such as a fluoroscopic video. The pose of fluoroscopic imaging device 124 relative to patient P while capturing the images may be estimated via markers incorporated with the transmitter mat 120. The markers are positioned under patient P, between patient P and operating table 112 and between patient P and a radiation source or a sensing unit of fluoroscopic imaging device 124. The markers incorporated with the transmitter mat 120 may be two separate elements which may be coupled in a fixed manner or alternatively may be manufactured as a single unit. Fluoroscopic imaging device 124 may include a single imaging device or more than one imaging device.

Computing device 122 may be any suitable computing device including a processor and storage medium, wherein the processor is capable of executing instructions stored on the storage medium. Computing device 122 may further include a database configured to store patient data, CT data sets including CT images, fluoroscopic data sets including fluoroscopic images and video, fluoroscopic 3D reconstruction, navigation plans, and any other such data. Although not explicitly illustrated, computing device 122 may include inputs, or may otherwise be configured to receive, CT data sets, fluoroscopic images/video and other data described herein. Additionally, computing device 122 includes a display configured to display graphical user interfaces. Computing device 122 may be connected to one or more networks through which one or more databases may be accessed.

With respect to a planning phase, computing device 122 utilizes previously acquired CT or MM image data for generating and viewing a three-dimensional model or rendering of patient P's airways, enables the identification of a target on the three-dimensional model (automatically, semi-automatically, or manually), and allows for determining a pathway through patient P's airways to tissue located at and around the target. More specifically, CT images acquired from previous CT or MM scans are processed and assembled into a three-dimensional volume, which is then utilized to generate a three-dimensional model of patient P's airways. The three-dimensional model may be displayed on a display associated with computing device 122, or in any other suitable fashion. Using computing device 122, various views of the three-dimensional model or enhanced two-dimensional images generated from the three-dimensional model are presented. The enhanced two-dimensional images may possess some three-dimensional capabilities because they are generated from three-dimensional data. The three-dimensional model may be manipulated to facilitate identification of target on the three-dimensional model or two-dimensional images, and selection of a suitable pathway through patient P's airways to access tissue located at the target can be made. Once selected, the pathway plan, three-dimensional model, and images derived therefrom, can be saved and exported to a navigation system for use during the navigation phase(s).

With respect to the navigation phase, a six degrees-of-freedom electromagnetic locating or tracking system 114, or other suitable system for determining position and orientation of a distal portion of the catheter 102, is utilized for performing registration of the images and the pathway for navigation. Tracking system 114 includes the tracking module 116, a plurality of reference sensors 118, and the transmitter mat 120 (including the markers). Tracking system 114 is configured for use with a locatable guide 110 and particularly sensor 104. As described above, locatable guide 110 and sensor 104 are configured for insertion through catheter 102 into patient P's airways (either with or without bronchoscope 108) and are selectively lockable relative to one another via a locking mechanism.

Transmitter mat 120 is positioned beneath patient P. Transmitter mat 120 generates an electromagnetic field around at least a portion of the patient P within which the position of a plurality of reference sensors 118 and the sensor 104 can be determined with use of a tracking module 116. A second electromagnetic sensor 126 may also be incorporated into the end of the catheter 102. The second electromagnetic sensor 126 may be a five degree-of-freedom sensor or a six degree-of-freedom sensor. One or more of reference sensors 118 are attached to the chest of the patient P. Registration is generally performed to coordinate locations of the three-dimensional model and two-dimensional images from the planning phase, with the patient P's airways as observed through the bronchoscope 108, and allow for the navigation phase to be undertaken with knowledge of the location of the sensor 104.

Registration of the patient P's location on the transmitter mat 120 may be performed by moving sensor 104 through the airways of the patient P. More specifically, data pertaining to locations of sensor 104, while locatable guide 110 is moving through the airways, is recorded using transmitter mat 120, reference sensors 118, and tracking system 114. A shape resulting from this location data is compared to an interior geometry of passages of the three-dimensional model generated in the planning phase, and a location correlation between the shape and the three-dimensional model based on the comparison is determined, e.g., utilizing the software on computing device 122. In addition, the software identifies non-tissue space (e.g., air filled cavities) in the three-dimensional model. The software aligns, or registers, an image representing a location of sensor 104 with the three-dimensional model and/or two-dimensional images generated from the three-dimension model, which are based on the recorded location data and an assumption that locatable guide 110 remains located in non-tissue space in patient P's airways. Alternatively, a manual registration technique may be employed by navigating the bronchoscope 108 with the sensor 104 to pre-specified locations in the lungs of the patient P, and manually correlating the images from the bronchoscope to the model data of the three-dimensional model.

Though described herein with respect to EMN systems using EM sensors, the instant disclosure is not so limited and may be used in conjunction with flexible sensor, ultrasonic sensors, or without sensors. Additionally, the methods described herein may be used in conjunction with robotic systems such that robotic actuators drive the catheter 102 or bronchoscope 108 proximate the target.

In accordance with the disclosure, the catheter 102 and its articulation and orientation relative to a target is achieved using a catheter drive mechanism 300. One example of such a drive mechanism can be seen in FIG. 3A which depicts a housing including three drive motors to manipulate a catheter extending therefrom in 5 degrees of freedom (e.g., left, right, up, down, and rotation). Other types of drive mechanisms including fewer or more degrees of freedom and other manipulation techniques may be employed without departing from the scope of the disclosure.

As noted above, FIG. 3 depicts a drive mechanism 300 housed in a body 301 and mounted on a bracket 302 which integrally connects to the body 301. The catheter 102 connects to and in one embodiment forms an integrated unit with internal casings 304a and 304b and connects to a spur gear 306. This integrated unit is, in one embodiment rotatable in relation to the housing 301, such that the catheter 102, internal casings 304 a-b, and spur gear 306 can rotate about shaft axis "z". The catheter 102 and integrated internal casings 304 a-b are supported radially by bearings 308, 310, and 312. Though drive mechanism 300 is described in detail here, other drive mechanisms may be employed to enable a robot or a clinician to drive the catheter to a desired location without departing from the scope of the disclosure.

An electric motor 314R, may include an encoder for converting mechanical motion into electrical signals and providing feedback to the computing device 122. Further, the electric motor 314R (R indicates this motor if for inducing rotation of the catheter 102) may include an optional gear box for increasing or reducing the rotational speed of an attached spur gear 315 mounted on a shaft driven by the electric motor 314R. Electric motors 314LR (LR referring to left-right movement of an articulating portion 317 of the catheter 102) and 314UD (referring to up-down movement of the articulating portion 317), each motor optionally includes an encoder and a gearbox. Respective spur gears 316 and 318 drive up-down and left-right steering cables, as will be described in greater detail below. All three electric motors 314 R, LR, and UD are securely attached to the stationary frame 302, to prevent their rotation and enable the spur gears 315, 316, and 318 to be driven by the electric motors.

Figure 3A:
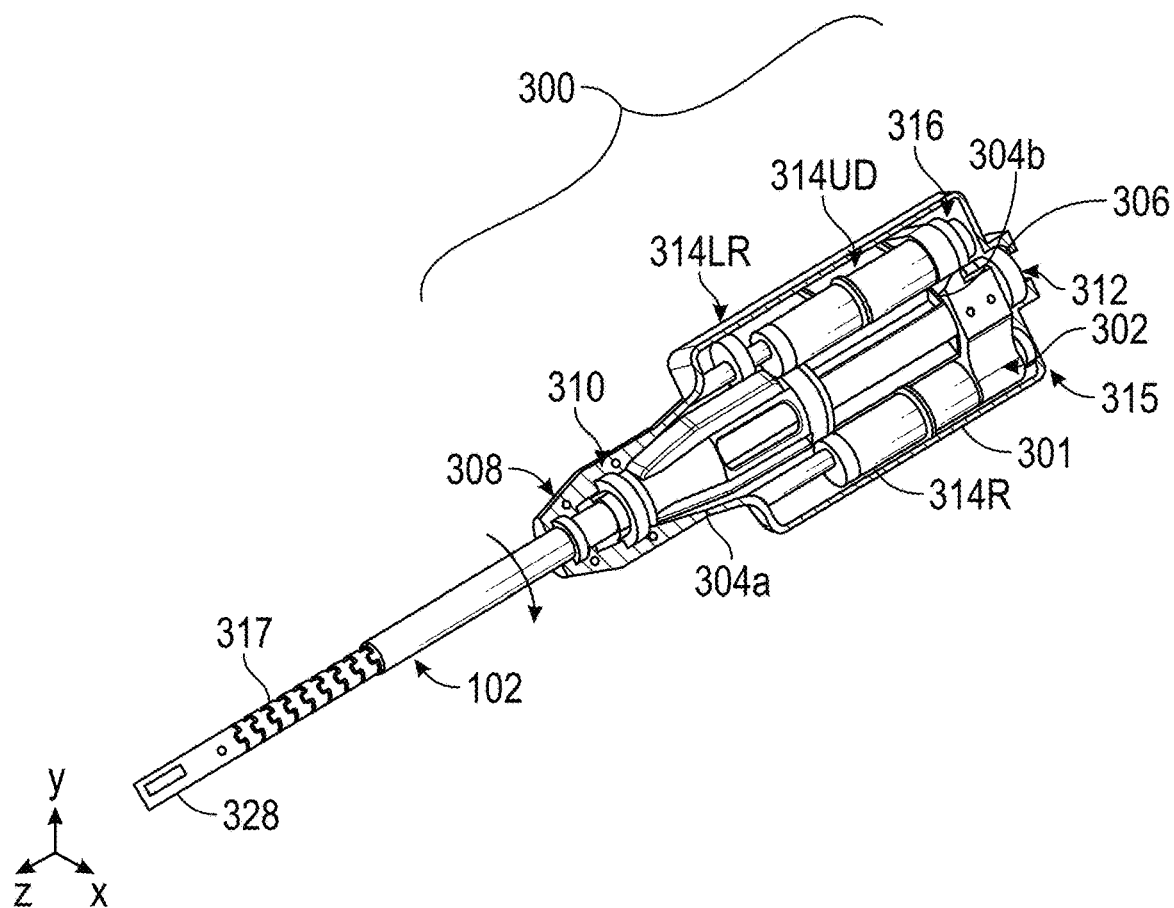
FIGS. 3A and 3B depict aspects of an articulation system for a catheter in accordance with the disclosure.
Figure 3B:
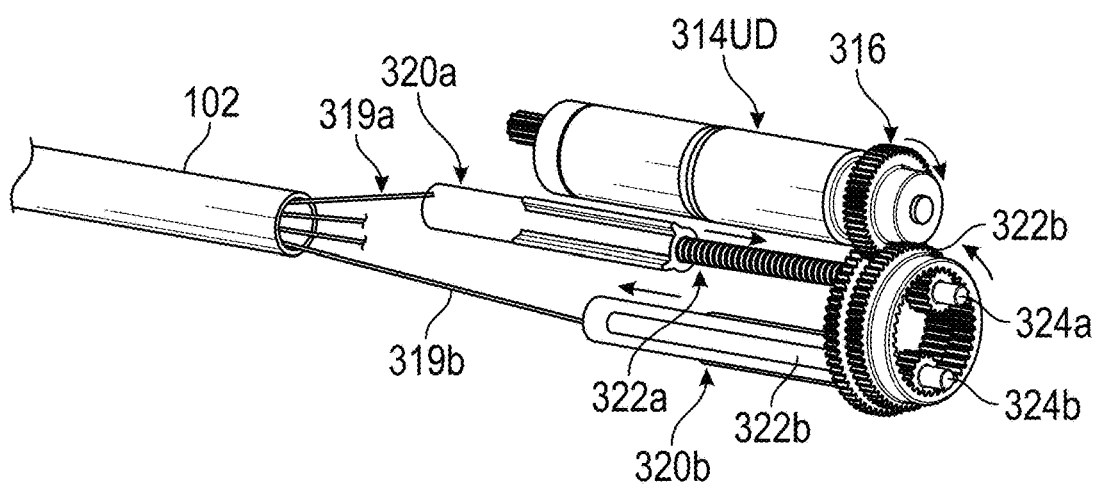
Figure 4:
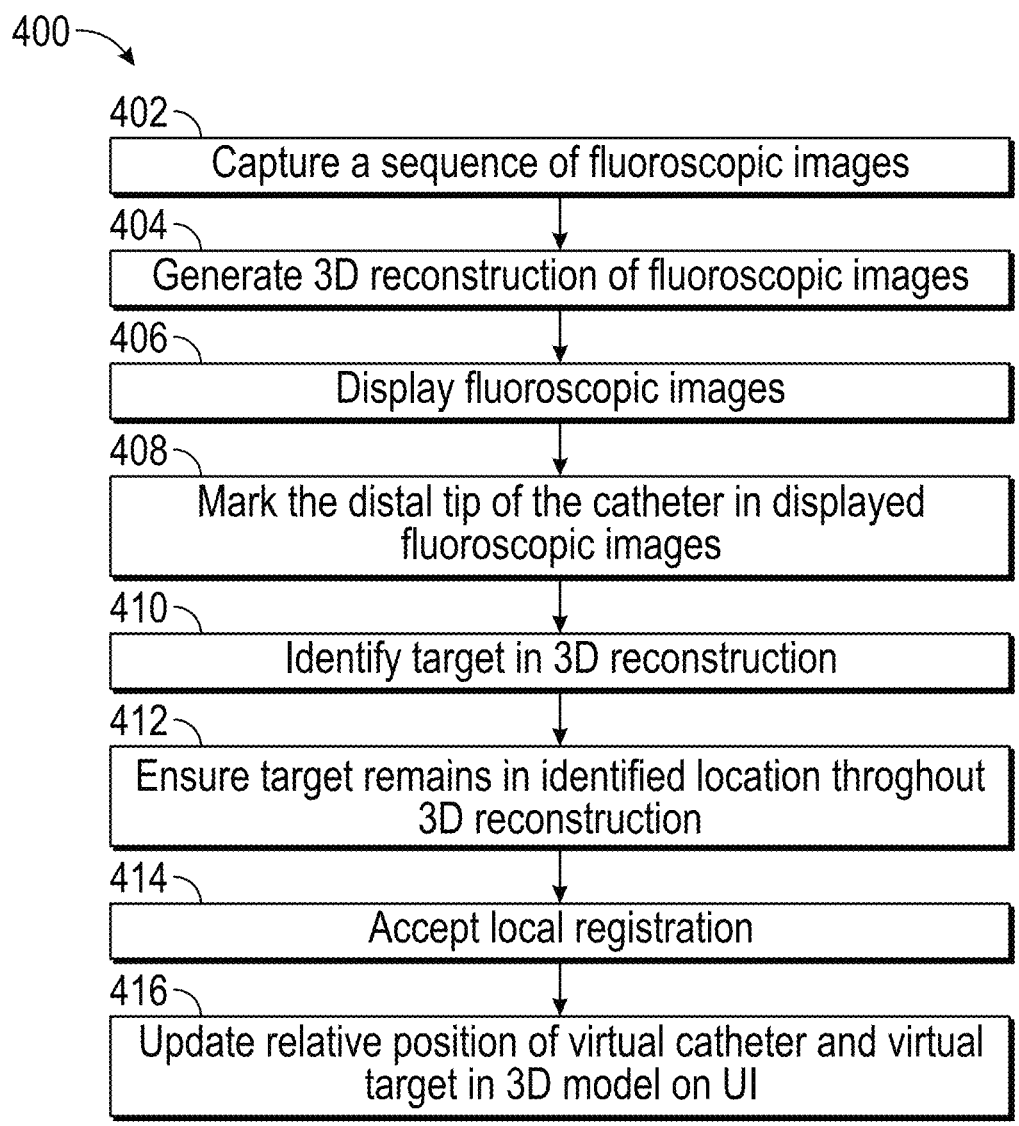
FIG. 4 is a flow chart of a method of local registration in accordance with the disclosure.

FIG. 3B depicts details of the mechanism causing articulating portion 317 of catheter 102 to articulate. Specifically, the following depicts the manner in which the up-down articulation is contemplated in one aspect of the disclosure. Such a system alone, coupled with the electric motor 314UD for driving the spur gear 1216 would accomplish articulation as described above in a two-wire system. However, where a four-wire system is contemplated, a second system identical to that described immediately hereafter, can be employed to drive the left-right cables. Accordingly, for ease of understanding just one of the systems is described herein, with the understanding that one of skill in the art would readily understand how to employ a second such system in a four-wire system. Those of skill in the art will recognize that other mechanisms can be employed to enable the articulation of a distal portion of a catheter and other articulating catheters may be employed without departing from the scope of the disclosure.

To accomplish up-down articulation of the articulating portion 317 of the catheter 102, steering cables 319 a-b may be employed. The distal ends of the steering cables 319 a-b are attached to, or at, or near the distal end of the catheter 102. The proximal ends of the steering cables 319 a-b are attached to the distal tips of the posts 320 a, and 320 b. As shown in FIG. 12, the posts 320a and 320b reciprocate longitudinally, and in opposing directions. Movement of the posts 320 a causes one steering cable 319 a to lengthen and at the same time, opposing longitudinal movement of post 320b causes cable 319b to effectively shorten. The combined effect of the change in effective length of the steering cables 319 a-b is to cause joints a forming the articulating portion 317 of catheter 102 shaft to be compressed on the side in which the cable 319b is shortened, and to elongate on the side in which steering cable 319 a is lengthened.

The opposing posts 320 a and 320 b have internal left-handed and right-handed threads, respectively, at least at their proximal ends. As shown in FIG. 13 housed within casing 304 b are two threaded shafts 322 a and 322 b, one is left-hand threaded and one right-hand threaded, to correspond and mate with posts 320 a and 320 b. The shafts 322 a and 322 b have distal ends which thread into the interior of posts 320a and 320a and proximal ends with spur gears 324a and 324bb. The shafts 322 a and 322 b have freedom to rotate about their axes. The spur gears 324 a and 324 b engage the internal teeth of planetary gear 326. The planetary gear 326 also an external tooth which engage the teeth of spur gear 318 on the proximal end of electric motor 314UD.

To articulate the catheter in the upwards direction, a clinician may activate via an activation switch (not shown) for the electric motor 314UD causing it to rotate the spur gear 318, which in turn drives the planetary gear 326. The planetary gear 326 is connected through the internal gears 324 a and 324 b to the shafts 322 a and 322 b. The planetary gear 326 will cause the gears 324 a and 324 b to rotate in the same direction. The shafts 322 a and 322 b are threaded, and their rotation is transferred by mating threads formed on the inside of posts 320 a and 320 b into linear motion of the posts 320 a and 320 b. However, because the internal threads of post 320 a are opposite that of post 320 b, one post will travel distally and one will travel proximally (i.e., in opposite directions) upon rotation of the planetary gear 326. Thus, the upper cable 319 a is pulled proximally to lift the catheter 102, while the lower cable 319 b must be relaxed. As stated above, this same system can be used to control left-right movement of the end effector, using the electric motor 314LR, its spur gear 316, a second planetary gear (not shown), and a second set of threaded shafts 322 and posts 320 and two more steering cables 319. Moreover, by acting in unison, a system employing four steering cables can approximate the movements of the human wrist by having the three electric motors 314 and their associated gearing and steering cables 319 computer controlled by the computing device 122.

Though generally described above with respect to receiving manual inputs from a clinician as might be the case where the drive mechanism is part of a hand-held catheter system, the disclosure is not so limited. In a further embodiment, the drive mechanism 300 is part of a robotic system for navigating the catheter 102 to a desired location within the body. In accordance with this disclosure, in instances where the drive mechanism is part of a robotic catheter drive system, the position of the distal portion of the catheter 102 may be robotically controlled.

The drive mechanism may receive inputs from computing device 122 or another mechanism through which the surgeon specifies the desired action of the catheter 102. Where the clinician controls the movement of the catheter 102, this control may be enabled by a directional button, a joystick such as a thumb operated joystick, a toggle, a pressure sensor, a switch, a trackball, a dial, an optical sensor, and any combination thereof. The computing device responds to the user commands by sending control signals to the motors 314. The encoders of the motors 314 provide feedback to the control unit 24 about the current status of the motors 314.

In accordance with the disclosure, and as outlined in greater detail below, the drive mechanism 300 receives signals derived by the computing device 122 to drive the catheter 102 (e.g., extend and retract pull-wires) to maintain the orientation of the distal tip of the catheter 102 despite extension of a tool such as a biopsy needle or ablation catheter or movements caused by respiration and cardiac cycles.

As described in connection with FIGS. 3A and 3B, catheter 102 is operated on its proximal end through a collection of controls for rotation and distal tip deflection. In contrast, to the embodiment described in connection with FIGS. 3A and 3B, a manually advanced catheter 102 may not include the motor 314R, relying instead on manual manipulation for rotation of the catheter 102. Alternatively, the drive mechanism may include only a single wire 319, or a single pair of wires 319a, 319b. In such an embodiment, articulation is enabled in a single or in a pair of wires in opposite directions. One or more knobs or levers or wheels on the proximal handle control or energize the energize the respective motor 314 to enable for distal tip articulation. Rotation and advancement/extraction of the catheter 102 are controlled directly by the user's hand pushing, pulling and rotating the catheter 102 within the patient. As described in connection with FIGS. 3A and 3B, any or all of these manual controls can be removed, and users indirectly control the catheter operation through an interface to the motors such as a joystick. Navigation may also be fully automatic with user oversight.

Figure 2:
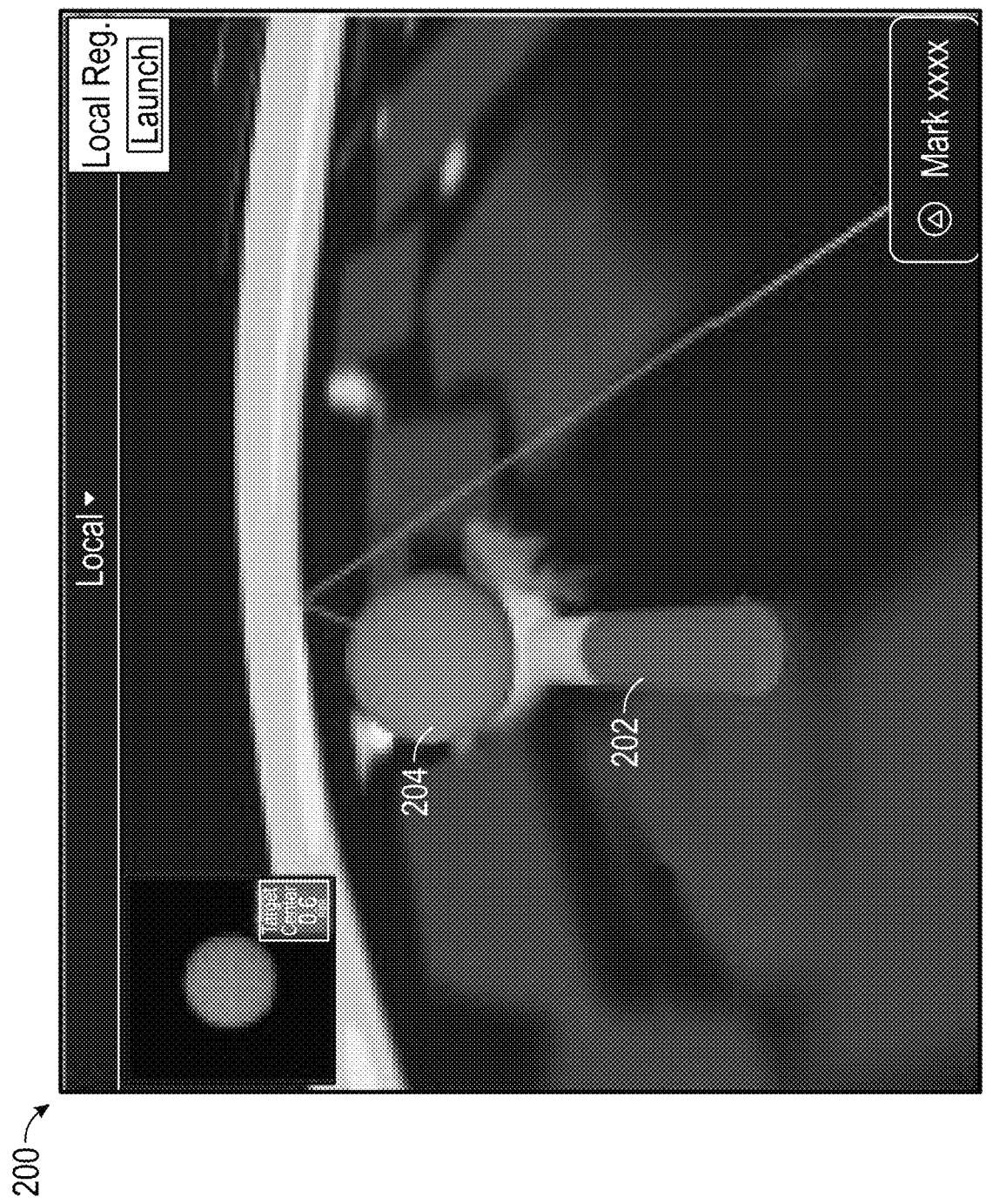
FIG. 2 is a user interface in accordance with the disclosure.

Following planning, registration, and then navigation of a catheter 102 proximate the target, a user interface (UI) 200 on computing device 122 may depict an image as seen in FIG. 2. UI 200 depicts a rear perspective view of a virtual distal tip 202 of catheter 102. The position of the virtual distal tip 202 relative to the virtual target 204 is displayed in the UI 200. This displayed position is based on the detected position of the catheter 102, and more particularly the sensors 104, 126 relative to the location of the target as identified in the pre-procedure scan from which the 3D model as derived. This relative position relies on the registration to provide accuracy. However, whether manual or robotic, as noted above, the pathway plan and 3D model developed from the pre-procedure scan data must be registered to the patient before navigation of the catheter to a target within the anatomy can being.

Accordingly, a local registration process operating on computing device 122 may be employed. In accordance with the local registration process, once catheter 102 has been successfully navigated proximate, as shown in FIG. 2, the target 202 a local registration process 400 may be performed for each target to reduce the CT-to-body divergence. An initial step 402 a sequence of fluoroscopic images is captured via fluoroscopic imaging device 124 for example from about 30 degrees on one side of the AP position to about 30 degrees on the other side of the AP position. At step 404 a fluoroscopic 3D reconstruction may be then generated by the computing device 122. The generation of the fluoroscopic 3D reconstruction is based on the sequence of fluoroscopic images and the projections of structure of markers incorporated with transmitter mat 120 on the sequence of images. Following generation of the fluoroscopic 3D reconstruction, two fluoroscopic images are displayed on computing device 122 at step 406. At step 408 the distal tip of the catheter 102 is marked in each of these images. The two images are taken from different portions of the fluoroscopic 3D reconstruction. The fluoroscopic images of the 3D reconstruction may be presented on the user interface in a scrollable format where the user is able to scroll through the slices in series if desired.

Next at step 410 the target needs to be identified in the fluoroscopic 3D reconstruction. In one example, the clinician will be asked to mark the target in two different perspectives of the 3D reconstruction. At step 412, the entire fluoroscopic 3D reconstruction may be viewed to ensure that the target remains within an identified location, such as a circle placed on the target throughout the fluoroscopic 3D reconstruction. At step 414 the local registration can be accepted. At step 416 the relative position of the virtual catheter 202 in the 3D model relative to the virtual target 204 is updated to display the actual current relative position of the end of the catheter 102 and the target calculated by the local registration process 400. By the local registration process the offset between the location of the target and the tip of the catheter 102 is determined as they are observed in the fluoroscopic 3D reconstruction. The offset is utilized, via computing device 122, to correct any errors in the original registration process and minimize any CT-to-body divergence. As a result, the location and or orientation of the navigation catheter on the GUI with respect to the target is updated. At this point the clinician has a high degree of confidence in the position of the catheter 102 relative to the target as displayed in the UI 200.

By the process described above the relative positions of the catheter 102 and the target are marked in the 3D fluoroscopic reconstruction and the offset determined. In addition, the position of the catheter 102 is always being sensed either in the EM field to provide EM coordinates of its position, or in robotic coordinates if a robot is employed. The offset can then be used to update the position of the virtual distal tip 202 in UI 200 relative to the virtual target 204. Thus improving the registration and providing a clearer indication of the relative positions of the virtual distal tip 202 and virtual target 204, that more closely depicts the actual relative positions of the distal tip of the catheter 102 and the target in the patient.

While far improved, the local registration process 400 does not account for movement of the catheter 102 or the target caused by respiration or heartbeat. Further, after the local registration process, the clinician or robot will typically remove the LG 110 with sensor 104 from the catheter 102 and insert a medical device in the catheter 102 and advance the medical device towards the target. As will be appreciated, in addition to the effects of respiration and heartbeat the relative positions of the catheter 102 and the target can be affected by the removal of the LG and the insertion of other tools. Thus, while the local registration is an improvement and overcomes the CT to body divergence, it is necessarily a static update to the relative positions of the catheter 102 and the target.

As noted above, maintaining distal tip location and orientation to the target is difficult as the patient's body is moving due to pulmonary and cardiac activity along with muscle motion and disturbances cause by external forces such as the surgical staff moving the patient. Additional motion can be caused by motion of equipment around the patient such as surgical bed or anesthesia tube motion. These motions cause external forces that can alter the amount of distal tip articulation of the catheter 102, cause the catheter 102 to move forward or backward, or impart rotational forces on the catheter 102. If the catheter 102 is used as a tool to interact with the target location such as a lesion or is used to deploy a tool through a lumen in the catheter, the target anatomy can distort or move due to pressure from the tool deployment. As an example, deployment of a needle to perform biopsy on a lesion adjacent to a bronchial tube can result in movement of the catheter 102. The action of the needle perforating the stiffer, cartilage-like airway can distort the softer lung tissue behind causing both the lesion and the catheter 102 to move and the needle miss. Thus, the 3D model and the sensed position of the catheter 102, as depicted in FIG. 2, even after a local registration process 400 cannot be relied upon to confirm that the tip of the catheter 102 is oriented towards (i.e., pointed at a target) at any particular time, and further that the tip of the catheter 102 remains in this orientation when tools are inserted therethrough for biopsy and treatment of the target.

A further aspect of the disclosure is directed to the use of an inertial measurement unit (IMU) within catheter 102. For some of these applications the IMU 328 may be configured as a small microchip measuring as little as 2 mm×2 mm in size and less than 1 mm in thickness. As will be appreciated, such a small size makes IMUS very useful in medical navigation applications in accordance with the disclosure. However, other size devices may be employed without departing from the scope of the disclosure.

An IMU 328 is a sensor typically including one or more accelerometers, and one or more gyroscopes. Additionally, an IMU 328 may include one or more of a magnetometer, a pressure sensor, and other types of sensors. An IMU 328 provides individual velocity and acceleration measurements in the X, Y, and Z directions as well as roll about the X, Y, and Z axes. Using trigonometric operations, these measurements can be converted into a directional vector showing which way the IMU 238 is moving. Combining two vectors allows for calculation of distance traveled. While the effects of gravity need to be compensated for at all times, the gravity vector can be used to identify the orientation of the sensor. Identification of the orientation of the IMU 328 provides an indication of the orientation of the catheter 102. Thus, this in addition to using the local registration process 400 to determine the location of the distal portion of the catheter 102 relative to the target, the IMU 328 can be utilized to determine an orientation of the distal tip of the catheter 102.

Figure 5:
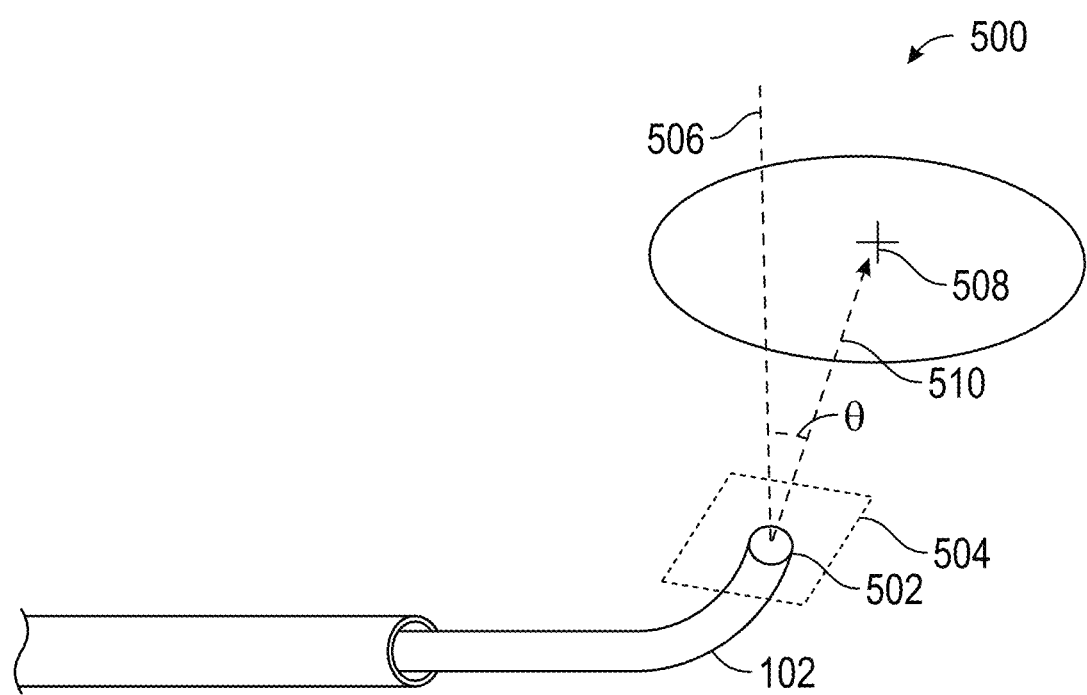
FIG. 5 is view as may appear on a user interface depicting the orientation of a distal portion of a catheter relative a target.

FIG. 5 depicts a catheter 102 as it may appear on a UI 500 following navigation proximate a target. By including an IMU 328 in the distal portion of the catheter 102, the plane 502 defined by the opening 504 in the end of the catheter 102 can be determined using an application running on the computing device 122. The plane 502 which coincides with the opening 504 allows for determination of a vector 506 which as depicted in FIG. 5 is normal to a plane 502 transverse to the length of the catheter 102. The vector 506 depicts the path that a tool, such as a biopsy or treatment tool, extended from the opening 504 at the distal end of the catheter 102 would follow if extended from the distal tip of the catheter 102. As can be seen in FIG. 5, the vector 506 does not coincide with a vector from the catheter 102 to the target 508, thus a tool extended from the catheter would miss the target 508. The angle θ represents the 3D angle of change in orientation of the distal tip of the catheter 102 required to have plane 502 oriented such that its orientation is such that a vector 510 extending normal to the plane 502 intersects the target 508.

A further aspect of the use of an IMU 328 is that its movement can be tracked throughout its navigation through the luminal network. As such, the effects of physiological forces from respiration and cardiac function can be detected and isolated from the overall movement of the catheter 102. In a sense, the IMU 328 can act as both a respiration rate monitor and a heart rate monitor. In some instances, this may require a pause to the navigation process to allow for collection of movement data while the catheter 102 is not otherwise being moved.

With collection of the physiological data such as heart rate and respiration rate, the movement of the distal portion of the catheter 102 caused by these physiological functions can be determined and tracked by the application running on computing device 122. Tracking can occur throughout the navigation process and the estimates of the movement caused by each force applied to the catheter 102 (e.g. motor force, hand manipulation, tissue responsive forces, and physiological forces) can be calculated and updated throughout navigation. And once proximate a target, as depicted in FIG. 5 the movement caused by the physiological data can be further refined and utilized as described in greater detail below.

As will be understood by those of skill in the art, even with motorized control as depicted in FIGS. 3A and 3B, known systems have difficulty in maintaining the orientation of the distal tip of the catheter 102 with respect to the target. In fact, known systems are generally not concerned with orientation of the catheter 102, but rather focus on maintaining the position and location or the articulation of the catheter. This is typically done through the use of sensors such as EM sensors or shape sensors. These known systems detect changes in the position or articulation of the distal tip and seek to counteract that movement through use of the motors to return the catheter 102 to the desired shape or to return the catheter 102 a desired position. However, such designs do not account for anatomic changes where the target's location in space is moving independent of any movement of the distal tip of the catheter 102. Rather these systems seek to maintain the position of the catheter 102 as determined in, for example, EM coordinates. But typically, there are no EM coordinates for the target, and more importantly there is no ability to utilize EM coordinates to track movement of the target. Still further, the entire patient, or at least a significant portion of them is also moving meaning that not only is the location of the target moving because of the physiological forces, but in fact the entire or a substantial portion of the entire patient.

A further aspect of the disclosure is directed to a method of addressing the above-identified shortcoming of prior catheter navigation systems. As described above, the method 600 may optionally start at step 602 with navigating a catheter 102 into a luminal network of a patient. This navigation may be manual or robotically driven and may follow a pre-planned pathway through a 3D model derived from pre-procedure images such as CT images. Further, prior to the onset of navigation the 3D model may be registered to the patient as described above. Those of skill in the art will recognize that method 600 may also begin after navigation and commence with step 604 wherein IMU 328 associated with the catheter 102 collects data related to movement of the catheter. This data regarding movement of the catheter 102, and particularly the IMU 328 enables determination of both respiration and heart rate data and the movements caused by the physiological forces. As an optional step 606, a UI on a display of computing device 122 may prompt the user to "Stop movement" of the catheter 102, allowing the IMU to collect just the physiological movement data (e.g., that caused by heartrate, breathing, and other internal muscular contractions of the patient).

After reaching a desired proximity to a target 508 at step 608, for example between 2 and 5 CM from the target for example based on detection of the position of the catheter via the EM sensor 104, a fluoroscopic sweep is acquired of the end of the catheter 102 and the target 508 at step 610. Following the process described above, the end of the catheter 102 and the target 508 are marked in images derived from the fluoroscopic sweep at step 612. At step 614 the orientation of the distal tip of the catheter 102 is determined based on the data received from the IMU 328. At step 616 the application determines whether the orientation of the distal tip of the catheter 102 is such that a vector perpendicular to a plane 502 defined by the opening 504 in the distal tip is pointed at the target 508. If the answer is no, at step 618 the application running on computing device 122 can signal the motors 314 to adjust the articulation of the catheter 102 to achieve the correct orientation based a 3D angle between the vector 506 that does not intersect the target 508 and a vector 510 that would intersect the target 508. As an alternative the computing device 122 may provide an output in a UI on a display of the computing device of the movement necessary to achieve an orientation of the opening 504 such that the vector traverses the target. If the answer is yes, the method proceeds to step 620, where the movement data collected by the IMU relating the heart rate and respiration (as well as other muscle movements) is utilized by the application to provide drive signals to the motors 314 of the catheter 102 to maintain the orientation of the opening 504 relative to the target.

At step 622, if other operations are undertaken such as removal of the LG or insertion of a biopsy needle, the position and orientation of the catheter 102 is maintained by the application running on computing device 122. The IMU 328 outputs signals relating to its orientation which is associated with the orientation of the plane 502 at the of opening 504 of the catheter 102. When movement of the IMU 328 is detected, based on these user activities the application running on the computing device 122 generates signals to the motors 314 to adjust the shape of the distal portion of the catheter 102 to correct any change in orientation relative to the target.

Further, as part of step 622 the movements of the catheter 102 and particularly the IMU 328 caused by respiration and heartbeat can be detected. Because these are highly cyclical and repeated movements the application running on the computing device and generate signals which are sent to the motors 314 to adjustment the position of the distal portion of the catheter 102 such that opening 504 remains oriented at the target 500 throughout the cardiac and respiratory cycles.

The maintaining of the orientation of the distal end of the catheter 102 may be occur automatically, with drive signals being generated by computing device 122 and delivered to the motors 314 to counteract the movements of the distal tip of the catheter 102. Alternatively, the movement of the distal portion of the catheter 102 can be manually controlled either via switches, levers, or a wheel associated with the motors 314 to achieve the desired orientation of the opening 504 towards the catheter. The need for, the magnitude and the direction of these movements may be presented on a UI 200.

Whether manually initiated or controlled or partially controlled via computing device 122 the amount and speed of the movements the catheter 102 caused by the motors 314 can be gated based on the proximity to the target. Thus, when navigating the central airways or larger lumens larger movements of the end of the catheter 102 are possible. As the catheter 102 approaches a target 500, particularly a target located closer to the periphery of the lung or other bodily organ, the range of available movements of the distal portion of the catheter 102 may be reduced. This reduction can increase the safety of the movements particularly in the periphery of organs like the lungs. The determination of proximity of these locations may be based on the tracking system 114 employing the EM sensor 104 or a shape sensor, as described above.

Similarly, the amount of drift or error in orientation of the opening 504 in the catheter 104 towards the target 500 can be adjusted as desired by the user or to the limits of the processing power and speed of the computing device 122. Where a user desires continual movement of the catheter 102 to confirm orientation the amount of acceptable drift can be reduced. Alternatively, if fewer movements are desired, for example due to the tissue being navigated, the acceptable drift can be increased, and the signals will be sent from the computing deice 122 to the motors 314 less frequently.

Still further, because of the cyclical nature of these physiological forces, the application running on the computing device can anticipated the application of forces on the catheter 102 and begin application of compensating signals at a timing to ensure proper orientation at all times.

In one embodiment, the representations of the virtual catheter tip 202 and target 204 can be seen to move in the images displayed in the UI 200 in concert with the physiological signals. The images may be live fluoroscopic images, 3D model images from the pre-procedure imaging and pathway plan, or other imaging modalities. In an embodiment where the UI 200 displays 3D model images the viewer is afforded a virtual image of the reality of the movements occurring within the patient. In the UI 200 in this embodiment the distal portion of the virtual catheter tip 202 may be seen to flex to maintain the orientation towards the virtual target 204.

In a further embodiment, the UI 200 may include an indicator. For example, a portion of the UI 200 may have a portion which either changes brightness or changes color (e.g., from red to yellow to green). Alternatively, movements caused by respiration and cardiac function can be graphed over time, and portions of the graph may include a color indicator or include a color band. The indicator can be timed relative to the cardiac and respiratory forces applied to the catheter 102. Despite the articulation of the catheter 102 to maintain the orientation of the opening 504 towards the target 500, in some circumstances either the user may find it desirable to or the application running on computing device 122 can be configured to limit the timing of the use of tools to only those portions of the cyclical movement caused by the physiological forces that correspond to the approximate timing in the respiratory and cardiac cycle of when the fluoroscopic images were acquired. By performing this gating, a further confirmation that despite the movement of the target and the catheter 102, and even though the IMU 328 has been utilized to articulate the catheter 102, the catheter 102 and the target at these portions of the cardiac and respiratory cycle are now substantially at the same locations (e.g., in the same phase of the cardiac and respiratory cycle) as when the original orientation confirmation was acquired.

In a further aspect of the disclosure, the imaging system for identification of the catheter 102 and the target could be an ultrasound system, computed tomography (CT) system, cone beam CT system, MRI system or another capable system of imaging both the catheter 102 and the target simultaneously. Further, though described herein as occurring just once, the external imaging (e.g., fluoroscopy, ultrasound,) may be repeated at intervals during the procedure to ensure continued orientation of the catheter tip and the target. Still further, thought described herein as being identified by a user viewing the fluoroscopic or ultrasound images to determine the location and orientation of the catheter 102 relative to the target and the location of the target, these systems and methods described herein may additionally or alternatively employ automatic identification methods. Such automatic methods may use image processing software to automatically identify the distal tip and its orientation from the imaging system output.

Still further, in embodiments of the disclosure the maintaining of orientation of the distal tip of the catheter 102 and the target is a feature that can be turned on and off by the user or automatically whenever the catheter is greater than a preset distance from the target. Still further, the UI 200 may include an indicator to alert the user if the orientation lock between the catheter 102 and the target is ever lost. Such a feature may also indicate that the external imaging needed to be renewed so that the method 600 can be started a new. As will be appreciated, this orientation lock may be turned may be selectively turned on or off as desired by the user or by the application running on computing device 120.

Figure 6:
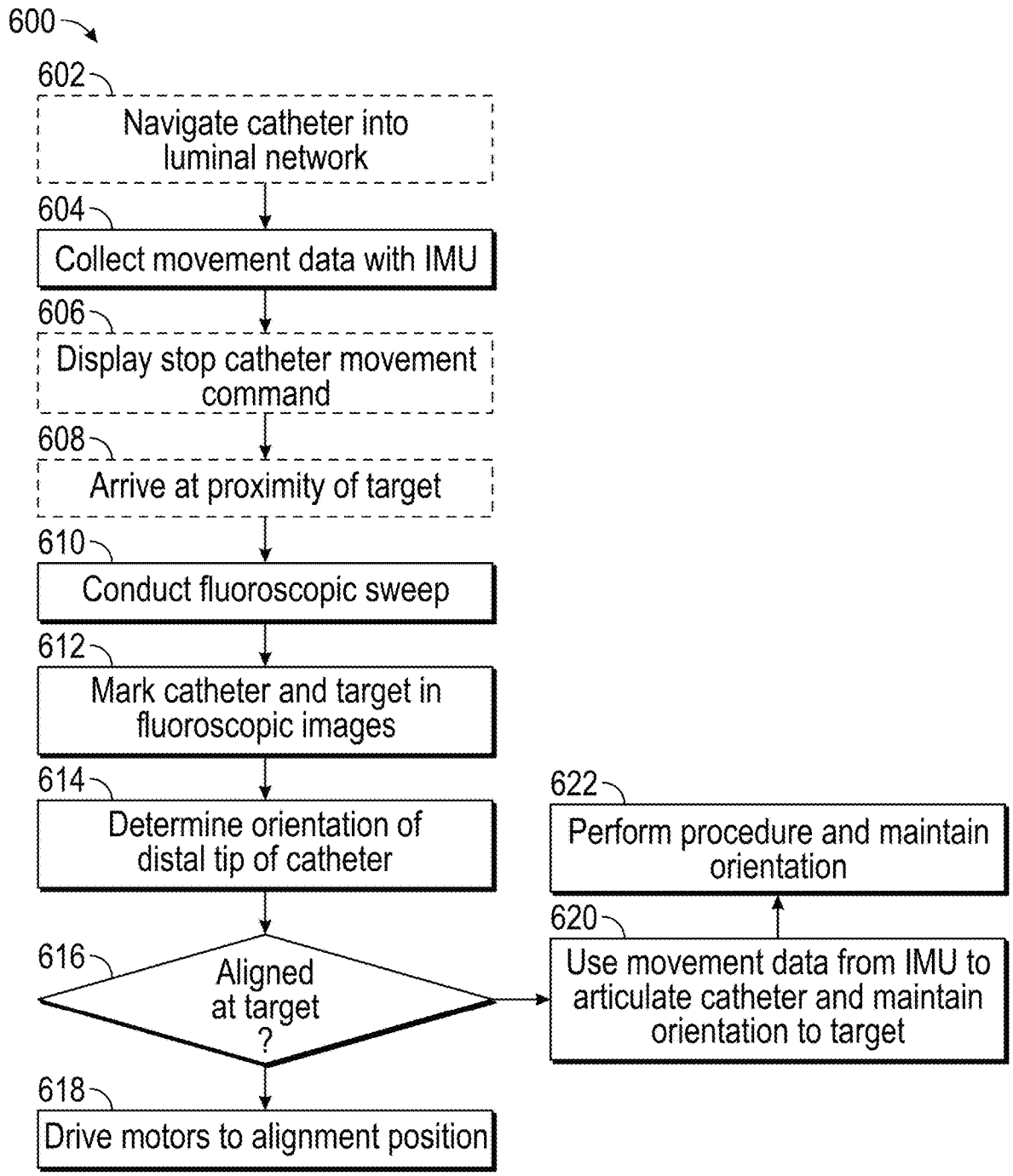
FIG. 6 is a flow chart describing a method of achieving and maintaining orientation of a distal portion of a catheter and a target.
Figure 7:
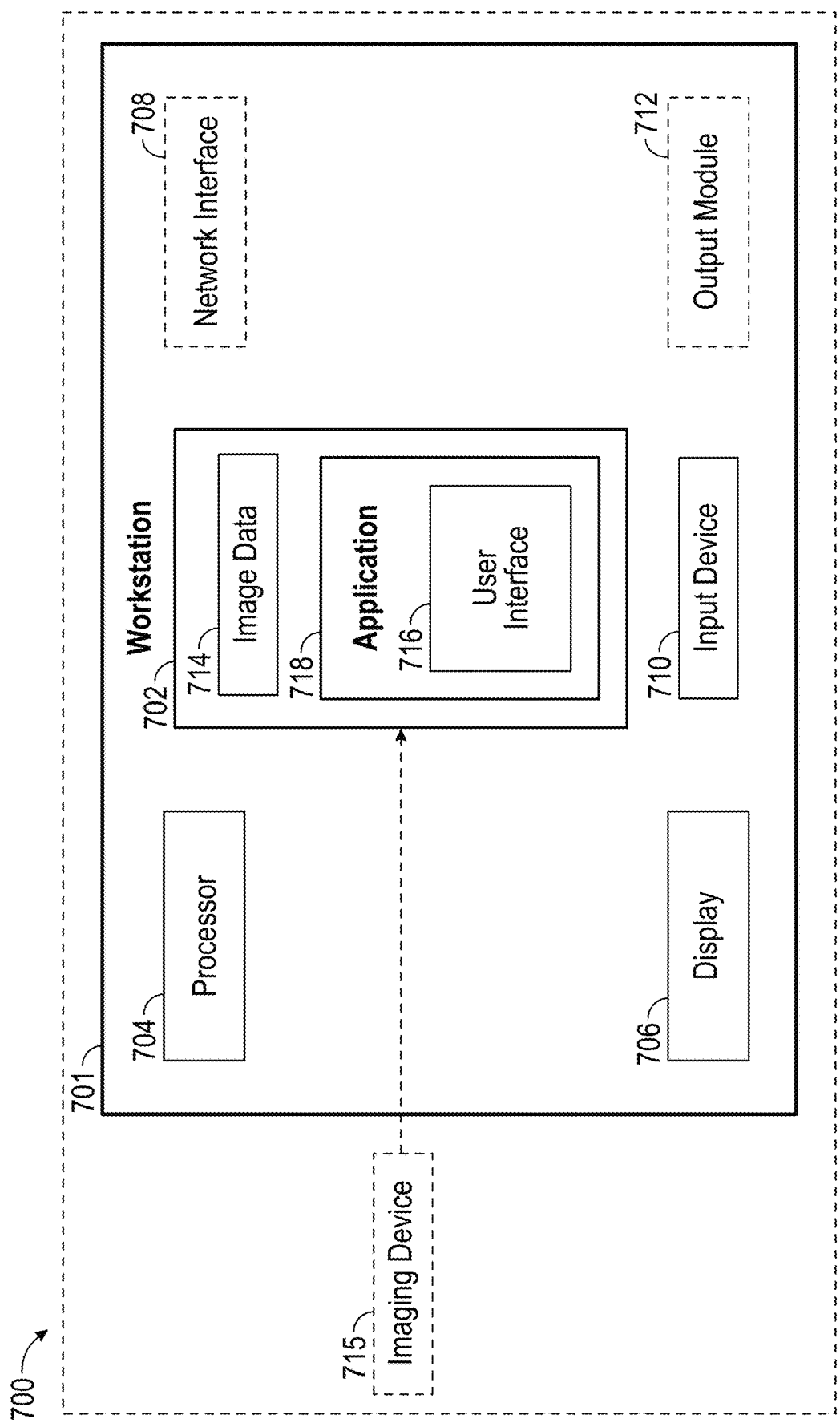
FIG. 7 is a schematic view of an imaging and computing system in accordance with the disclosure.

Reference is now made to FIG. 7, which is a schematic diagram of a system 700 configured for use with the methods of the disclosure including the method of FIG. 6. System 700 may include a workstation 701, and optionally an imaging device 715 (e.g., a fluoroscope or an ultrasound device). In some embodiments, workstation 701 may be coupled with imaging device 715, directly or indirectly, e.g., by wireless communication. Workstation 701 may include a memory 702, a processor 704, a display 706 and an input device 710. Processor or hardware processor 704 may include one or more hardware processors. Workstation 701 may optionally include an output module 712 and a network interface 708. Memory 702 may store an application 718 and image data 77. Application 718 may include instructions executable by processor 704 for executing the methods of the disclosure including the method of FIG. 6.

Application 718 may further include a user interface 716. Image data 714 may include the CT scans, the generated fluoroscopic 3D reconstructions of the target area and/or any other fluoroscopic image data and/or the generated one or more slices of the 3D reconstruction. Processor 704 may be coupled with memory 702, display 706, input device 710, output module 712, network interface 708 and imaging device 715. Workstation 701 may be a stationary computing device, such as a personal computer, or a portable computing device such as a tablet computer. Workstation 701 may embed a plurality of computer devices.

Memory 702 may include any non-transitory computer-readable storage media for storing data and/or software including instructions that are executable by processor 704 and which control the operation of workstation 701 and, in some embodiments, may also control the operation of imaging device 715. Imaging device 715 may be used to capture a sequence of fluoroscopic images based on which the fluoroscopic 3D reconstruction is generated and to capture a live 2D fluoroscopic view according to this disclosure. In an embodiment, memory 702 may include one or more storage devices such as solid-state storage devices, e.g., flash memory chips. Alternatively, or in addition to the one or more solid-state storage devices, memory 702 may include one or more mass storage devices connected to the processor 704 through a mass storage controller (not shown) and a communications bus (not shown).

Although the description of computer-readable media contained herein refers to solid-state storage, it should be appreciated by those skilled in the art that computer-readable storage media can be any available media that can be accessed by the processor 704. That is, computer readable storage media may include non-transitory, volatile and non-volatile, removable and non-removable media implemented in any method or technology for storage of information such as computer-readable instructions, data structures, program modules or other data. For example, computer-readable storage media may include RAM, ROM, EPROM, EEPROM, flash memory or other solid-state memory technology, CD-ROM, DVD, Blu-Ray or other optical storage, magnetic cassettes, magnetic tape, magnetic disk storage or other magnetic storage devices, or any other medium which may be used to store the desired information, and which may be accessed by workstation 1001.

Application 718 may, when executed by processor 704, cause display 706 to present user interface 716. User interface 716 may be configured to present to the user a single screen including a three-dimensional (3D) view of a 3D model of a target from the perspective of a tip of a medical device, a live two-dimensional (2D) fluoroscopic view showing the medical device, and a target mark, which corresponds to the 3D model of the target, overlaid on the live 2D fluoroscopic view. An example of the user interface 716 is shown, for example, in FIG. 2. User interface 716 may be further configured to display the target mark in different colors depending on whether the medical device tip is aligned with the target in three dimensions.

Network interface 708 may be configured to connect to a network such as a local area network (LAN) consisting of a wired network and/or a wireless network, a wide area network (WAN), a wireless mobile network, a Bluetooth network, and/or the Internet. Network interface 708 may be used to connect between workstation 701 and imaging device 715. Network interface 708 may be also used to receive image data 714. Input device 710 may be any device by which a user may interact with workstation 701, such as, for example, a mouse, keyboard, foot pedal, touch screen, and/or voice interface. Output module 712 may include any connectivity port or bus, such as, for example, parallel ports, serial ports, universal serial busses (USB), or any other similar connectivity port known to those skilled in the art. From the foregoing and with reference to the various figures, those skilled in the art will appreciate that certain modifications can be made to the disclosure without departing from the scope of the disclosure.

While detailed embodiments are disclosed herein, the disclosed embodiments are merely examples of the disclosure, which may be embodied in various forms and aspects. For example, embodiments of an electromagnetic navigation system, which incorporates the target overlay systems and methods, are disclosed herein; however, the target overlay systems and methods may be applied to other navigation or tracking systems or methods known to those skilled in the art. Therefore, specific structural and functional details disclosed herein are not to be interpreted as limiting, but merely as a basis for the claims and as a representative basis for teaching one skilled in the art to variously employ the disclosure in virtually any appropriately detailed structure.

What is claimed is:

1. A system for maintaining orientation of a catheter relative to a target, comprising:
    a catheter configured to generate signals relating to movement of a distal portion of the catheter; and
    a computing device, the computing device including a processor and a memory, the memory storing thereon instructions that when executed by the processor:
        receive signals from the catheter relating to movement of the distal portion of the catheter;
        isolate from the received signals, a portion of the received signals indicative of movement of the distal portion of the catheter caused by physiological forces;
        receive images depicting the distal portion of the catheter and a target;
        identify the distal portion of the catheter and the target in the images;
        confirm that the distal portion of the catheter is proximate to the target;
        determine an orientation of the distal portion of the catheter relative to the target; and
        articulate the distal portion of the catheter in response to a portion of the received signals indicative of movement of the distal portion of the catheter caused by physiological forces to achieve and maintain an orientation of the distal portion of the catheter towards the target during movement of the distal portion of the catheter caused by physiological forces such that a tool extended from an opening at the distal portion of the catheter would intersect the target.

2. The system according to claim 1, wherein the orientation of the distal portion of the catheter is determined using image analysis.

3. The system according to claim 1, further comprising the memory storing thereon further instructions, that when executed by the processor, determine a three-dimensional angle between a current orientation of the distal portion of the catheter and an orientation where a vector extending from the distal portion of the catheter intersects the target.

4. The system according to claim 3, further comprising the memory storing thereon further instructions, that when executed by the processor, articulate the distal portion of the catheter to achieve the orientation where the vector extending from the distal portion of the catheter intersects the target.

5. The system according to claim 1, wherein the images are fluoroscopic or ultrasound images.

6. The system according to claim 1, wherein the physiological forces are caused by respiration and cardiac functions.

7. The system according to claim 1, wherein the received signals are during navigation of the catheter towards the target.

8. The system according to claim 1, further comprising the memory storing thereon further instructions, that when executed by the processor, present on a user interface a virtual catheter tip and a virtual target.

9. The system according to claim 8, further comprising the memory storing thereon further instructions, that when executed by the processor, present an indicator on the user interface when the physiological forces are in approximately the same phase of their cycle as when the distal portion of the catheter was confirmed oriented at the target.

10. A system for maintaining orientation of a catheter relative to a target, comprising:
    a catheter configured to navigate within a luminal network; and
    a computing device, the computing device including a processor and a memory, the memory storing thereon instructions that when executed by the processor:
        isolate from a detected movement of a distal portion of the catheter a portion of the movement caused by physiological forces on the distal portion of the catheter;
        receive images depicting the distal portion of the catheter and a target;
        identify the distal portion of the catheter and the target in the images;

confirm that the distal portion of the catheter is proximate to the target;
determine an orientation of the distal portion of the catheter relative to the target; and
articulate the distal portion of the catheter in response the isolated portion of the movement of the distal portion of the catheter caused by physiological forces on the distal portion of the catheter to achieve and maintain an orientation of the distal portion of the catheter towards the target during the detected movement of the distal portion of the catheter caused by physiological forces when the distal portion of the catheter is proximate to the target.

11. The system according to claim 10, wherein the orientation of the distal portion of the catheter is determined using image analysis.

12. The system according to claim 10, further comprising the memory storing thereon further instructions, that when executed by the processor, determine a three-dimensional angle between a current orientation of the distal portion of the catheter and an orientation where a vector extending from the distal portion of the catheter intersects the target.

13. The system according to claim 10, wherein the physiological forces are caused by respiration and cardiac functions.

14. The system according to claim 10, further comprising the memory storing thereon further instructions, that when executed by the processor, determine a cyclic timing of the movement of the distal portion of the catheter due to physiological forces.

15. The system according to claim 10, further comprising the memory storing thereon further instructions, that when executed by the processor, detect, based on the detected movement of the catheter due to physiological forces, a heart rate and a respiration rate.

16. A system for maintaining orientation of a catheter towards a target, comprising:
a catheter;
a computing device, the computing device including a processor and a memory, the memory storing thereon instructions that when executed by the processor:
isolate, during navigation of the catheter within a luminal network, a portion of a detected movement of a distal portion of the catheter caused by physiological forces;
receive images depicting the distal portion of the catheter and a target;
confirm, based on the received images, that the distal portion of the catheter is proximate to the target;
determine an orientation of the distal portion of the catheter relative to the target; and
articulate the distal portion of the catheter in response to the isolated portion of the detected movement of the distal portion of the catheter caused by physiological forces to achieve and maintain an orientation of the distal portion of the catheter towards the target during the detected movement of the distal portion of the catheter caused by physiological forces when the distal portion of the catheter is proximate to the target.

17. The system according to claim 16, wherein the orientation of the distal portion of the catheter is determined using image analysis.

18. The system according to claim 16, further comprising the memory storing thereon further instructions, that when executed by the processor, determine a three-dimensional angle between a current orientation of the distal portion of the catheter and an orientation where a vector extending from the distal portion of the catheter intersects the target.

19. The system according to claim 16, wherein the physiological forces are caused by respiration and cardiac functions.

20. The system according to claim 16, further comprising the memory storing thereon further instructions, that when executed by the processor, determine a cyclic timing of the movement of the distal portion of the catheter due to physiological forces.

* * * * *